United States Patent [19]

Steinfort et al.

[11] Patent Number: 4,850,869

[45] Date of Patent: Jul. 25, 1989

[54] REMOVABLE DENTAL PROSTHESIS

[75] Inventors: Peter Steinfort, Düsseldorf; Gilbert Weis, Essen, both of Fed. Rep. of Germany

[73] Assignee: Fried.Krupp Gesellschaft mit beschräankter Haftung, Essen, Fed. Rep. of Germany

[21] Appl. No.: 911,917

[22] Filed: Sep. 26, 1986

[30] Foreign Application Priority Data

Sep. 28, 1985 [DE] Fed. Rep. of Germany ....... 3534751

[51] Int. Cl.$^4$ ............................................ A61C 13/225
[52] U.S. Cl. ................................. 433/172; 433/182; 433/193
[58] Field of Search ............... 433/180, 181, 182, 183, 433/192, 193, 194, 172

[56] References Cited

U.S. PATENT DOCUMENTS

| | | | |
|---|---|---|---|
| 1,211,494 | 1/1917 | Shaw | 433/181 |
| 1,621,702 | 3/1927 | Yantis | 433/181 |
| 3,787,975 | 1/1974 | Zuest | 433/182 |
| 4,609,355 | 9/1986 | Harvey, Sr. et al. | 433/181 |

FOREIGN PATENT DOCUMENTS

| | | | |
|---|---|---|---|
| 0131795 | 8/1932 | Austria | 433/183 |
| 0474206 | 9/1952 | Italy | 433/181 |
| 0508804 | 1/1955 | Italy | 433/183 |

Primary Examiner—John J. Wilson
Assistant Examiner—Adriene J. Lepiane
Attorney, Agent, or Firm—Spencer & Frank

[57] ABSTRACT

A dental prosthesis including a secondary member coupled to at least one prosthetic tooth suitable for being effectively mounted onto or readily removed from a primary member coupled to a remaining tooth or implant. A bar member is accommodated inside a common bore in the primary and secondary members for coupling thereof. An arresting disc member is introduced into a recess inside the prosthetic toth to block off a leading shaft portion of the bar member having the largest cross-section and preventing the bar member from falling out. The entire bar member is suitable for freely moving along the bores of the primary and secondary members. Between an intermediate portion of the bar member and the recess inside the prosthetic tooth is a space which is filled with plastic material. A trailing head portion of the bar member is ground off to correspond with the buccal exterior surface of the prosthetic tooth.

6 Claims, 2 Drawing Sheets

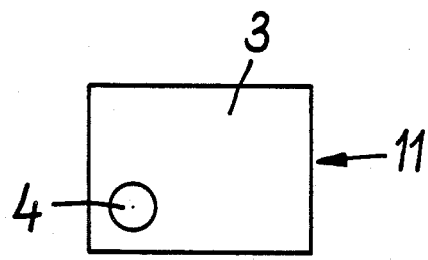
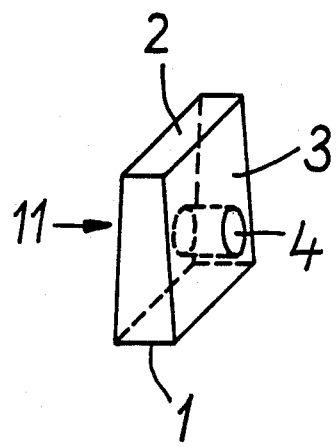
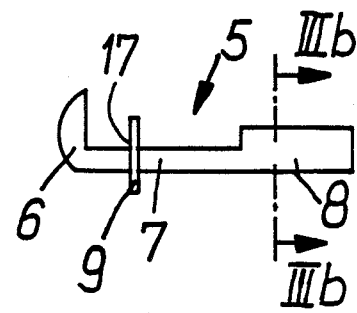

REMOVABLE DENTAL PROSTHESIS

BACKGROUND OF THE INVENTION

1. Field of the Invention

This invention relates to a removable dental prosthesis.

More particularly, the invention relates to a removable dental prosthesis which has a primary member coupled to a secondary member by the use of a bar member. The primary and secondary members have a common bore suitable for accommodating the bar member therein. The primary member is attached to at least one remaining tooth or with at least one associated implant while the secondary member is attached to at least one prosthetic tooth suitable for being coupled thereabove the primary member. The bar member which is accommodated inside the common bore is secured to the prosthetic tooth by an arresting member. An arresting box portion inside the secondary member is provided for holding a leading end of the bar member.

2. Description of Related Art

One method in the art of fastening or anchoring parts of a dental prosthesis to a remaining tooth is a so-called shifting arrangement. The best known non-activating shifting method is the T-shaped shifting mechanism which serves as a connector between a crown, a substantially large tooth filling or a similar supply element and a bridge post. The T-shaped shifting mechanism is made of a matrix provided with a trough and a matrix with a corresponding web which is suitable for being pushed over the matrix. The matrix is attached to the crown for example by soldering, while the patrix is fixed to the associated bridge post. Here, however, the pressing of the dental prosthesis against the remaining tooth requires a significant amount of work and great precision.

Further, there is available in the art dental prosthetic devices which are made of non-noble metal alloys. These devices include box-like primary and secondary members which are suitable for fitting together. Bores which have a common longitudinal axis, are drilled through the fully-assembled device by spark erosive processes. A sliding bar member is inserted from the lingual side of the device through the bore in order to form a releasable plug-in connection. Here, however, the drawbacks are obvious in that manufacturing costs are significantly high due to the implementation of the required spark erosion processes. Moreover, the trailing end of the sliding bar member is not made flush to enable the sliding bar member to be withdrawn from the lingual side of the prosthetic device, frequently causing the tongue of a patient to be constantly rubbed and irritated.

SUMMARY OF THE INVENTION

It is an object of the present invention to provide an improved dental prosthesis apparatus and a method for connecting thereof.

It is another object of the present invention to provide primary and secondary members coupled to the improved dental prosthesis which may be removable coupled to at least one remaining tooth or with at least one corresponding implant.

It is still another object of the present invention to provide the secondary member of the improved dental prosthesis with a permanent and durable outside connecting surface for effective mating thereof with at least one remaining tooth or with at least one corresponding implant.

It is yet another object of the present invention to provide an easily inserted and readily replaceable bar member for sturdily connecting the primary and secondary members together.

It is a further object of the present invention to provide the bar member with a trailing end which can be easily ground off until flush with the abutting outside surface of the prosthesis.

It is a further object of the present invention to provide an improved dental prosthesis which can be easily installed, require few parts and sufficiently rigid when in use.

It is yet a further object of the present invention to provide an improved dental prosthesis which is comfortable, inexpensive and easy to manufacture.

The above and other objects are achieved, according to the invention, in a method for producing a removable dental prosthesis composed of a primary member permanently connected to a supporting dental structure in the mouth of a patient, a secondary member arranged to be placed over the primary member so as to cover the primary member, a prosthetic tooth secured to the secondary member the primary and secondary members and the prosthetic tooth having openings which are mutually aligned when the secondary member is in position around the primary member, a slide bar arranged to seat in the openings for anchoring the members together, and a supporting member for engaging the prosthetic tooth, which method includes:

forming the primary member by forming an elongate body of a removable material constituting a model of the primary member, connected to a wax-model of a tooth removing the removable material by the known wax burn out process, and casting the primary member;

forming the secondary member by forming a body of a removable wax-material constituting a model of the secondary member, removing the removable material by the wax burn out process, and casting the secondary member;

forming the openings in the primary and secondary members;

providing the secondary member with a recess which is to be aligned with the openings when the secondary member is in position around the primary member and which is to receive one end of the slide bar;

providing the prosthetic tooth with a recess at the end of the opening therein which is remote from the secondary member for receiving the supporting member; and assembling the slide bar to the prosthetic tooth by inserting the slide bar into the opening in the prosthetic tooth, placing the supporting member onto the slide bar, and embedding the supporting member in the recess in the prosthetic tooth, by the improvement wherein:

the steps of forming the primary and secondary members comprise forming the openings in the primary and secondary members by providing the bodies of removable material with ceramic or Co-Cr-alloy-spacers corresponding to the openings, and casting the primary and secondary members with the spacers in place;

the step of providing the prosthetic tooth with a recess comprises drilling the recess from the associated exterior surface of the tooth; and the step of embedding comprises filling the recess with a filler material and causing the slide bar to be substantially flush with the exterior surface of the prosthetic tooth.

The objects according to the invention are further achieved in a dental prosthesis comprising:

a primary member permanently connectable to a supporting dental structure in the mouth of a patient, the primary member being provided with a bore;

a secondary member mountable over, and removably connectable to, the primary member, the secondary member having an opening and a recess which, when the secondary member is connected to the primary member, are located at opposite sides of the primary member and are aligned with the bore.

A prosthetic tooth having buccal and lingual surfaces and fastened to the secondary member, the tooth having a passage aligned with the opening in the secondary member and extending from the buccal surface;

a slide bar having leading and trailing ends and an intermediate position disposed between the ends, the slide bar being arranged to be inserted, when the secondary member is mounted over the primary member, through the passage in the tooth, the opening in the secondary member and the bore in the primary member, with the leading end seated in the recess in the secondary member and the trailing end being in the vicinity of the buccal surface of the tooth, for connecting the secondary member and the primary member together; and an arresting and bearing disc secured to the slide bar and embedded in the tooth when the slide is inserted, the improvement wherein:

the bore and the part of the slide bar in the bore have non-rotationally symmetrical cross sections, which prevent rotation of the slide bar relative to the primary member; and the trailing end of the slide bar is formed to be substantially flush with the buccal surface of the tooth when the slide bar is inserted with the leading end seated in the recess.

The foregoing and other objects, features and advantages of this invention will be apparent from the following, more particular, description of the preferred embodiments of this invention, as illustrated in the accompanying drawings.

BRIEF DESCRIPTION OF THE DRAWINGS

FIGS. 1 and 2 are a side view and a perspective view, respectively, of one embodiment of a primary member of an improved dental prosthesis in accordance with the present invention showing a bore or an aperture passing therethrough.

FIG. 3a is a side view of a bar member which has leading, intermediate and trailing portions with an arresting eye member suitable for sliding therealong the intermediate portion.

FIG. 3b is a cross-sectional view of the bar member taken in the direction of line IIIb—IIIb of FIG. 3a, illustrating how the leading portion is configured.

DESCRIPTION OF THE PREFERRED EMBODIMENTS

Figure 4A:
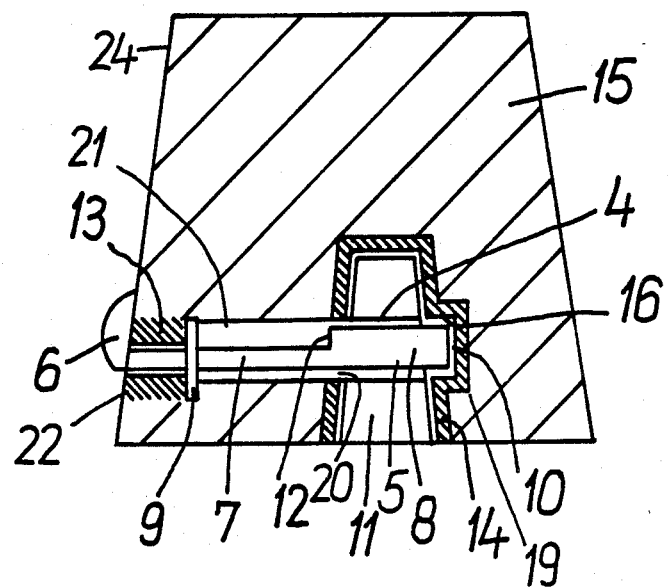
FIGS. 4a and 4b are cross-sectional views showing the manner in which the primary and secondary members are coupled to a prosthetic tooth with the bar member in a bolted state and unbolted state, respectively.

The primary member, generally referred to by reference number 11, illustrated in FIGS. 1 and 2 is composed of a flat, prismatic body having a base, or bottom face 1, top face 2 and major side faces 3, all faces 1, 2, 3 being substantially rectangular. The side faces 3 are inclined toward each other in a manner wherein the entire body becomes smaller toward the top portion; i.e., toward the side that will face away from the associated gingiva (not shown). In the lower third portion of primary member 11, and preferably near one edge, a bore, or aperture, 4, preferably having a maximum diameter of between 1.3 and 1.4 mm, passes therethrough, between side faces 3. This arrangement of bore 4 offers the advantage of permitting primary member 11 to be mass produced, thereby contributing to a significant cost reduction. Secondly, a plurality of primary members 11 can be manufactured in a uniform size which can then be cut to any desired lengths at the side remote from bore 4. Primary member 4 can then be secured to remaining tooth structure in a known manner.

As shown in FIG. 3a, a bar member 5 has a head portion 6, a leading shaft portion 8, and an intermediate shaft portion 7 therebetween. Intermediate shaft portion 7 has a smaller cross-sectional area than the leading shaft portion 8. Moreover, an arresting member 9, having an aperture 17 passing therethrough for accommodating the intermediate shaft portion 7 therein, is seated around portion 7 and serves to prevent bar member 5 from dropping out of the bore or aperture 4 of primary member 11 and out of a bore or an aperture 21 of a prosthetic tooth 15 (see FIGS. 4a and 4b). The arresting member 9 may be configured as a known circlip or the like.

FIG. 3b shows that the leading shaft portion 8 of bar member 5 has a semi-circular cross-sectional configuration which will prevent rotation of bar member 5 when inside corresponding bores or apertures 4, 20, 21 (see FIGS. 4a and 4b), or in a guide shaped in a wax melting process by means of spacers.

Figure 4B:
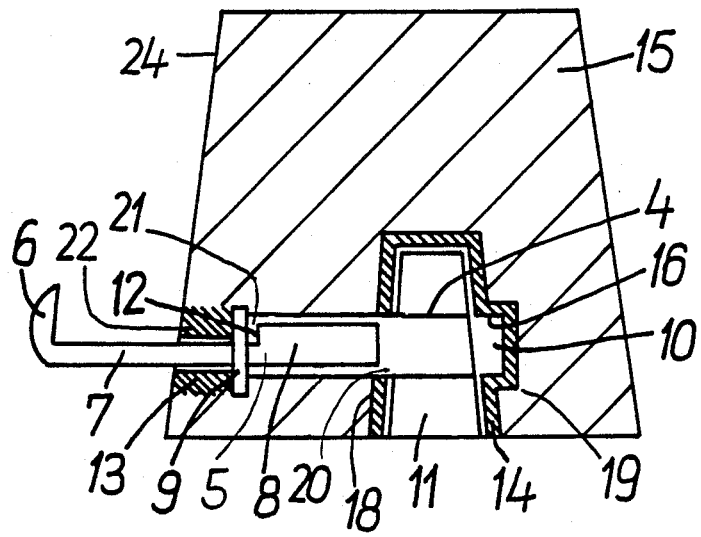

As shown in FIGS. 4a and 4b, a secondary member 14 is secured in and covered by a prosthetic tooth 15. The secondary member 14 is cast so that it can be pushed over and substantially cover the external surfaces of the primary member 11. Preferably on the buccal side 18, i.e. The side which will be directed toward the patient's cheek, secondary member 14 has a bore or aperture 20 passing therethrough which is in congruence with the corresponding bore or aperture 4 of the primary member 11 in order to accommodate the bar member 5. Moreover, secondary member 14 is provided, preferably on the internal face of its lingual side 19, with a receiving box-like portion or recess 10 for holding the free end of leading shaft portion 8 of the bar member 5. Alternatively, a guide face portion 16, also at the lingual side 19 of the secondary member 14, may be sufficient to secure the end of the leading shaft portion 8 of bar member 5.

The bores or apertures 4, 20 of primary member 11 and secondary member 14, respectively, as well as a bore or aperture 21 which passes through prosthetic tooth 15, from its buccal side 24, must be sufficiently large to allow the leading shaft portion 8 of bar member 5 to pass therethrough. An enlarged portion 22 of the bore or aperture 21 is provided for insulation of arresting member 9. Consequently, after bar member 5 has been inserted, a space remains between intermediate shaft portion 7 of bar member 5 and the wall of enlarged portion 22 of the bore or aperture 21. That space is then filled with plastic or filler material 13. Before filling the space with material 13, the bar member 5 is waxed (in the inserted state) in order for its free longitudinal mobility to remain in effect. Preferably, the head portion 6 of bar member 5 is then ground off until flush with the abutting surface of the buccal side 24 of the prosthetic tooth 15.

As further illustrated in FIG. 4b, when the leading shaft portion 8 of bar member is pulled out of the receiving box-like portion of the secondary member 14 and out of the bore or aperture 4 of the primary member 11, edge portion 12 of the transition from the larger leading shaft portion 8 to the intermediate shaft portion 7 having the smaller cross-sectional area ultimately comes to rest against the arresting member 9. Accordingly, it is not possible to pull the bar member 5 out further beyond the arresting member 9.

To form the connector according to the invention, initially a plastic or wax model is produced in the shape of a bar with an aperture extending transversely through its longitudinal axis in its lower portion, preferably, proximate its based portion. The plastic or wax model is connected to a tooth model with the use of wax. A ceramic or Co-Cr-alloy-spacer preferably having a non-rotationally symmetrical diameter, is inserted into the aperture before casting of the primary member 11. In other words, it is preferred that the aperture is already worked into the plastic or wax model and filled with the ceramic spacer before casting. Thereafter, the plastic or wax model is melted and the primary member 11 is cast.

The primary member 11 is preferably cut to the desired length by removing portions spaced from the bore or aperture 4, without affecting the bore or aperture 4 in any way. Thereafter, the primary member 11 can be fastened to remaining tooth structure (not shown) in a manner known in the art.

The secondary member is cast so as to be covered by the prosthetic tooth and is formed so that when later pushed over primary member 11 it will cover all surfaces of member 11.

Member 14 is cast in a manner similar to the casting of member 11 in that a plastic or wax model is formed and is provided with an opening corresponding to bore 20 and a recess corresponding to the receiving portion. The latter opening and recess are filled with spacers before the plastic wax is removed and the secondary member is cast.

Prosthetic tooth 15 can be similarly fabricated, using a spacer to form bore 21 and enlarged portion 22.

The receiving box-like portion 10 is formed during casting of the secondary member 14. The enlarged portion 22 of the bore or aperture 21 is preferably drilled into the finished prosthetic tooth 15 from the outside, preferably from its buccal side 24.

The improved dental prosthesis and the method for connecting thereof of the present invention can also be used for a so-called "switchable" prosthesis wherein the bar member 5 is preferably arranged at a point whereby the wearer can most easily manipulate it. In such an arrangement, chewing pressure is distributed by way of the primary member 11 to at least two of the remaining teeth (not shown). As further illustrated in FIGS. 4a and 4b, the chewing pressure is completely absorbed by the primary member 11 without any leverage acting on the bar member 5. In such an arrangement, no problem is posed in using the "switchable" prosthesis, even with a user having a cleft palate, and no increased stress on the bar member 5 results.

Preferably, plastic retainers (not shown) are placed from the outside onto the secondary member 14 so as to permit easy fastening of the prosthetic tooth 15.

According to a further feature of this invention, secondary member 14 is manufactured by a fill casting or infusion process; i.e., secondary member 14 is cast in a centrifugal casting process onto the primary member 11 after having formed a mixture of various alloy components of the primary 11 and secondary 14 members in the form of an oxide skin.

The Co-Cr-alloy-spacer contains 20–40% Cr, 2–12% Mo, up to 2% Si, up to 5% Mn, up to 1% C, 0.1–1% N, with the rest being Co.

Preferably the alloy has 63.5% Co, 28.5% Cr, 6% Mo, up to 1% Si, up to 0.35% C and up to 1% Mn.

The method for connecting the improved dental prosthesis of the present invention can be used for fastening a unilateral or a bilateral free-end prosthesis wherein the removable dental prosthesis is firmly and rigidly fastened to the remaining tooth in the patient's mouth. In particular, it is not necessary, as had frequently been the custom in recent decades, to require a plurality of complicated fastening mechanisms to fasten the prosthesis to the patient's remaining dental structure which sometimes requires clamps to be fastened to the remaining tooth which tends to damage the remaining tooth. The removable dental prosthesis with the connecting apparatus thereof can be produced without much laboratory work since mass produced standard parts can be employed for the primary members 11 and secondary members 14. As a whole, this method results in a considerable reduction of costs for dental prostheses.

All commercially available alloys, particularly, but not limited to, all non-noble metal alloys are suitable for the manufacture of the bar member 5. Since the bar member 5 is mounted on plastic in the removable prosthetic tooth 15, it can be replaced at any time in an economical manner.

The bar member 5 has a non-rotationally symmetrical cross section which prevents rotation in the common bores or apertures 4, 20, 21, of corresponding cross section, and is preferably inserted from the buccal side 24 of the prosthetic tooth 15 and into the primary 11 and secondary 14 members.

According to a further feature of the invention, the bore or aperture 4 accommodating the bar member 5 preferably has a maximum diameter between 1.3 and 1.5 mm, which has been found to be the ideal range. The bore or aperture 4 preferably lies in the lower third and at one of the ends of the bar-shaped primary member 11. The primary member 11 is also preferably tapered toward the side facing away from the gingiva (not shown). Non-noble metal alloys, in particular, are suitable materials for the primary 11 and secondary 14 members. The preferred material for the primary member 11 is an alloy preferably composed of 0.4 to 0.5% C, 0.7 to 1.0% Si, 1% Mn, 27 to 30% CR 4.5 to 5.0% Mo, 0.5% W, up to 1.0% Fe, remainder Co, and for the secondary member 14, an alloy preferably composed of 15 to 25% Cr, 3 to 6% Mo, 2 to 5% Ti, remainder Co. Both alloys are excellently suited to be processed together in a casting on technic or infusion process.

The bar-shaped primary member 11, as well as the secondary member 14, can be prefabricated in a uniform size and, when required, can be reduced in length as well as height. This is made possible primarily by locating bore 4 in the lower third and near one edge of member 11. This measure saves time and labor-intensive laboratory work. Due to the fact that the bar member 5 can be introduced and removed from the buccal side 24 of the prosthetic tooth 15, the bar member 5 is much easier to manipulate particularly by the patient himself. Additionally, the patient is not likely to be annoyed by the extension of the head portion 6 of the bar member 5 which rests on the buccal side 24 of the prosthetic tooth 15.

As a whole, the present invention provides an extracoronal web bar for releasably anchoring dental prostheses to the remaining teeth (not shown) while permitting easy removal of the secondary member 14 from the primary member 11 without the bar member 5 dropping out during the process. Due to the fact that the head portion 6 of the bar member 5 is securely disposed on the buccal region or side 24 and the intermediate portion 7 is imbedded in plastic material 13, the bar member 5 can also be economically replaced at any time. To do this, it is merely necessary to drill open the plastic material 13 to the extent that the bar member 5 and the arresting eye member 9 can be pulled out and replaced. The bar member 5 having the nonrotationally symmetrical cross-sectional configuration is placed in its guides in a non-rotatable manner so that the head portion 6 which is adapted to the external contours of the prosthetic teeth 15 does not constitute a projecting, annoying foreign object in the mouth.

The method for producing a removable dental prosthesis having a primary and a secondary member has the following steps.

First of all a gypsum-model of the situation (dental structure) in the mouth of the patient is produced. Then a wax-model is filled upon the grinded teeth and a primary wax-member is connected to the wax-model by modeling.

The primary wax-member is provided with a bore, in which a ceramic or metallic Co-Cr-alloy-spacer is placed. The wax-model with primary wax-member is connected to casting-chanels, taken from the gypsum-model and set up a funnel-former and then the pig-iron casting is produced by the well known wax burn out process.

The pig-iron casting is finished and the spacers are removed. Then the pig-iron casting is fitted on the gypsum-model.

After this a duplicate-model is produced.

Upon the primary member placed on the duplicate-model a secondary wax-member is modeled and a spacer is placed in the bore of the primary member and an opening in the secondary wax member. Then casting-channels are connected to the secondary wax member and the secondary pig-iron casting is produced by the wax burn out process, in the course of which the casting on-technic is applied.

The secondary pig-iron casting is finished and fitted on the primary member. After this the primary member is masked and upon the secondary member the teeth are put up and provided with a gypsum-pre-wall. The wax is burned out. Through the secondary member and the bore of the primary member a spacer is fitted, the pre-wall fixed and the teeth complained (finished) with plastic material. The spacers are removed, the opening in the prothetic tooth on the buccal side is widened and the slide bar put in. At last the arresting member is set up and the remaining space in the tooth is filled up with plastic material.

While the invention has been particularly shown and described in reference to preferred embodiments thereof, it will be understood by those skilled in the art that changes in form and details may be made therein without departing from the spirit and scope of the invention.

The present disclosure relates to the subject matter disclosed in German Pat. No., P 35 34 751.1 filed Sept. 28, 1986, the entire specification of which is incorporated herein by reference.

It will be understood that the above description of the present invention is susceptible to various modifications, changes and adaptations, and the same are intended to be comprehended within the meaning and range of equivalents of the appended claims.

What is claimed is:

1. In a dental prosthesis comprising:
   a primary member permanently connectable to a supporting dental structure in the mouth of a patient, said primary member being provided with a bore;
   a secondary member connected to said primary member, said secondary member having an opening and a recess which are located at opposite sides of said primary member and are aligned with said bore;
   a prosthetic tooth having buccal and lingual surfaces and fastened to said secondary member, said tooth having a passage aligned with said opening in said secondary member and extending from said buccal surface;
   a slide bar having leading and trailing ends and an intermediate position disposed between said ends, said slide bar being disposed through said passage in said tooth, said opening in said secondary member and said bore in said primary member, with said leading end seated in said recess in said secondary member and said trailing end being in the vicinity of said buccal surface of said tooth, thereby connecting said secondary member and said primary member together; and
   an arresting and bearing disc secured to said slide bar and embedded in said tooth, the improvement wherein:
   a part of said slide bar in said tooth and at least one of said bore, said passage and said opening have non-rotationally symmetrical cross sections, which prevent rotation of said slide bar relative to said primary member; and
   said trailing end of said slide bar is substantially flush with said buccal surface of said tooth.

2. Dental prosthesis as defined in claim 1 wherein said bore in said primary member has a maximum diameter of 1.3 to 1.5 mm.

3. Dental prosthesis as defined in claim 1 wherein said primary member has the form of a bar with lower and upper ends which, are directed, respectively, toward the gingiva of the patient and the crown of the tooth, and lateral sides extending between the upper and lower ends, and said bore is located in the lower third of said primary member, in the direction between said upper and lower ends, and adjacent one of said lateral sides.

4. Dental prosthesis as defined in claim 1 wherein said primary member has lower and upper ends which, are directed, respectively, toward the gingiva of the patient and the crown of the tooth, and said primary member is tapered from said lower end toward said upper end.

5. The dental prosthesis apparatus of claim 1 wherein said primary member and said secondary member are made of non-noble metal alloys.

6. The dental prosthesis apparatus of claim 1 wherein said primary member is composed of an alloy which comprises between 0.4 and 0.5% C, between 0.7 and 1.0% Si, 1% Mn, between 27 and 30% Cr, between 4.5 and 5.0% Mo, 0.5% W, no more than 1.0% Fe, and remainder Co, and said secondary member is composed of an alloy which comprises between 15 and 25% Cr, between 3 and 6% Mo, between 2 and 5% Ti, and remainder Co.

* * * * *